United States Patent [19]
Savourey et al.

[11] Patent Number: 5,865,762
[45] Date of Patent: Feb. 2, 1999

[54] MODULE FOR RECORDING THE INSTANTANEOUS HEART RATE AND PORTABLE MODULE FOR WORKING SAME

[75] Inventors: Gustave Savourey, Biviers; Richard Caterini, Orlienas, both of France

[73] Assignee: Etat Francais, Armees, France

[21] Appl. No.: 895,927

[22] Filed: Jul. 17, 1997

[30] Foreign Application Priority Data

Jul. 18, 1996 [FR] France .................................. 96 08993

[51] Int. Cl.⁶ .................................................. A61B 5/0456
[52] U.S. Cl. .......................................... 600/519; 600/513
[58] Field of Search .................................. 600/521, 483, 600/474, 502, 513, 519

[56] References Cited

U.S. PATENT DOCUMENTS 4,576,178  3/1986  Johnson .

FOREIGN PATENT DOCUMENTS 0 553 372 A1   8/1993   European Pat. Off. .
26 33 371      1/1978   Germany .

Primary Examiner—Scott M. Getzow
Attorney, Agent, or Firm—Oliff & Berridge, PLC

[57] ABSTRACT

The invention relates to a portable module for recording the cardiac activity of a person with the aid of a device delivering an ECG signal. The device includes a main energy source connected to a second energy source supplying a temperature sensor by a controlled circuit, a unit that picks up and processes an ECG signal, having an ECG signal filter stage, connected to two integrators with different time constants. The integrator outputs are connected to a comparator delivering a signal ($E_3$) representing cardiac cycles. The device also includes a mechanism for placing the ECG signal pickup and processing unit in operation and a processor.

17 Claims, 3 Drawing Sheets

MODULE FOR RECORDING THE INSTANTANEOUS HEART RATE AND PORTABLE MODULE FOR WORKING SAME

BACKGROUND OF THE INVENTION

1. Field of the Invention

The invention relates to the technical area of recording physiological and physical data of a patient so that, in particular, monitoring, screening, or diagnosis can be performed. The invention relates in particular to recording the electrical activity of the heart muscle of a patient and the temperature of the patient.

2. Description of Related Art

In the above technical area, numerous instruments are known that take the patient's temperature and, by use of cells placed on the body of a patient, send an electrocardiogram signal, known as ECG, corresponding to the electrical currents produced by heart muscle contractions. A range of instruments have been developed, with the drawback of being fixed and with limited independent operation, requiring data to be acquired at times that do not necessarily respond to a characteristic phase of the heart rhythm. Moreover, data are recorded when the person is under conditions that do not exactly reproduce actual situations in the patient's daily life. It thus appeared that an ambulatory device was needed, adapted to a patient, and designed for picking up both physical and physiological data over a period of several days to several weeks.

One of the drawbacks of ambulatory devices is their inaccuracy, because they cannot follow the instantaneous heart rate. Moreover, these devices have a short power supply life, limiting their utilization time.

SUMMARY OF THE INVENTION

The object of the invention is to remedy the above drawbacks by offering a method for recording the instantaneous heart rate of a patient, as well as the patient's temperature.

To achieve this object, the method according to the invention includes the steps of detecting the peaks of the ECG signal with two integrators having different time constants and connected to a comparator delivering a signal representing the cardiac cycles; recording the times of the cardiac cycles; and recording the temperature as soon as the start of the cardiac cycle is detected.

Another object of the invention is to provide a portable module for recording the instantaneous heart rate and temperature of the patient while also providing high operating autonomy.

According to the invention, the module includes a main energy source connected to a second energy source supplying the temperature sensor by a controlled circuit; a unit that picks up and processes the ECG signal, having an ECG signal filter stage, connected to two integrators with different time constants, the integrator outputs being connected to a comparator delivering a signal representing cardiac cycles; a mechanism for placing the ECG signal pickup and processing unit in operation; and a processor. The processor includes an analog-digital converter designed to receive the analog signal delivered by the temperature sensor; a counter to which the comparator output is connected to determine the times of the cardiac cycles; and a control unit allowing the circuit controlling the operation of the secondary energy source to be controlled and the times of the cardiac cycles and the associated temperature values to be recorded.

BRIEF DESCRIPTION OF THE DRAWINGS

These and other aspects and advantages of the invention will become apparent from the following detailed description of preferred embodiments when taken in conjunction with the accompanying drawings, in which.

DETAILED DESCRIPTION OF PREFERRED EMBODIMENTS

Figure 1:
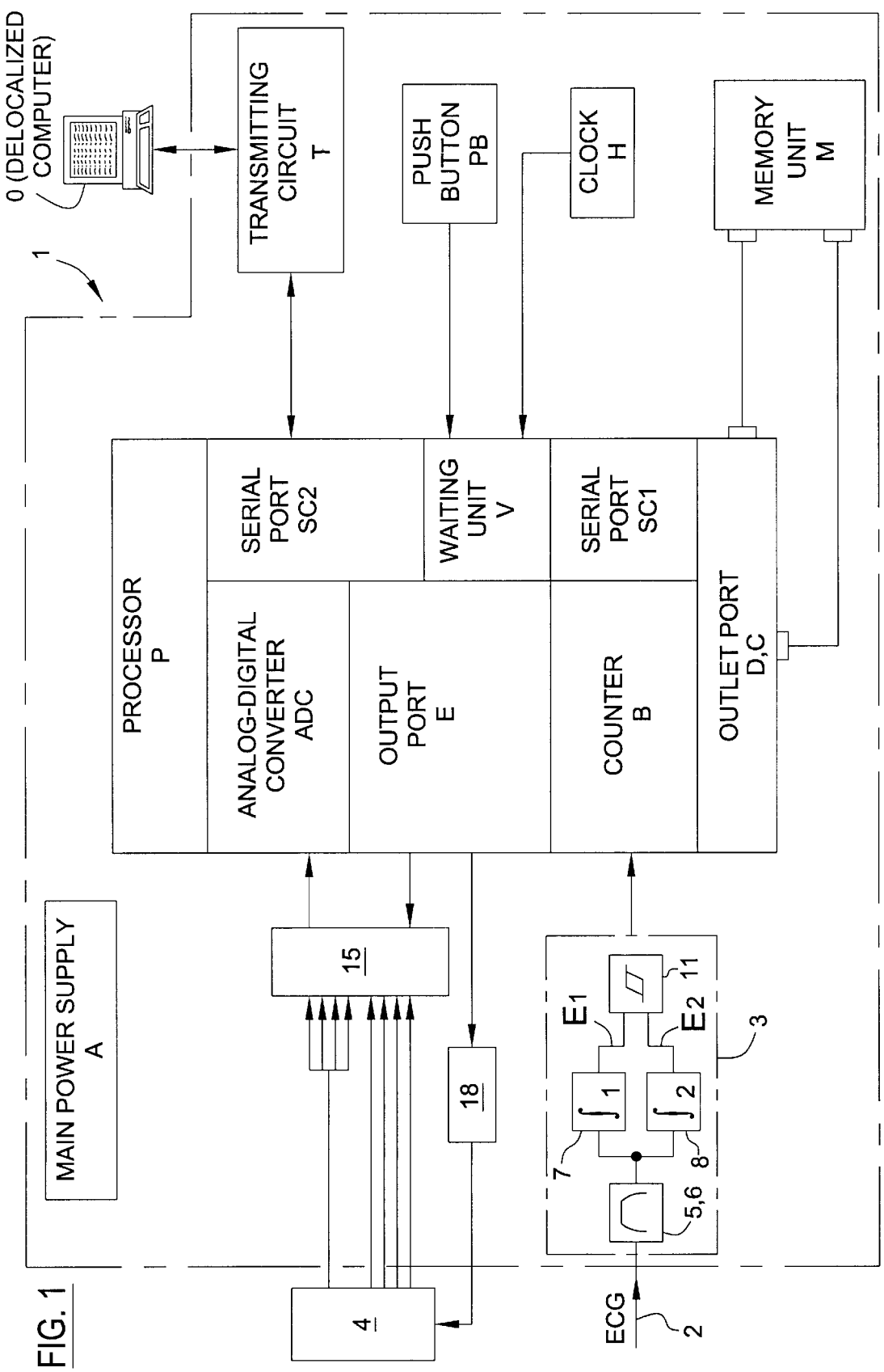
FIG. 1 is a block diagram illustrating the ambulatory module according to the invention.

While the invention will hereinafter be described in connection with preferred embodiments thereof, it will be understood that it is not intended to limit the invention to those embodiments. On the contrary, it is intended to cover all alternatives, modifications and equivalents that may be included within the spirit and scope of the invention as defined by the appended claims.

For a general understanding of the features of the invention, reference is made to the drawings. In the drawings, like reference numerals have been used throughout to designate identical elements.

As shown in FIG. 1, portable module 1 is designed to record the heart activity and temperature of a person. Module 1 is designed to be worn by a patient by any appropriate device, (not shown). Portable module 1 is designed to be connected to a known device (not shown) having electrodes placed on the patient so as to deliver an electrical signal produced by the heart muscle contractions. Such an electrocardiogram signal 2 (ECG), is received by a pickup and processing unit 3 which is part of module 1.

According to the invention, module 1 is designed to pick up at least one temperature from the patient simultaneously with the acquisition of the ECG signal. Module 1 is thus designed to be connected to sensors 4 placed such that, for example, one or more skin, esophageal, tympanic, or rectal temperatures can be taken.

Module 1 has a unit for processing and calculating the signals received and is designed around a processor P, for example of the PIC 16C74 type, made by Microchip Technology Inc. Module 1 also has a main power supply A that delivers a voltage of 3.6 V, for example, a memory unit M connected to outlet port D, C of processor P, a clock H connected to a serial port SC1 of the processor, and a transmitting circuit T connected to serial port SC2 of the processor and designed to be connected with a delocalized computer O by means of a link, for example RS232. Module 1 is also provided with a pushbutton PB connected to a waiting unit V of processor P.

Figure 2:
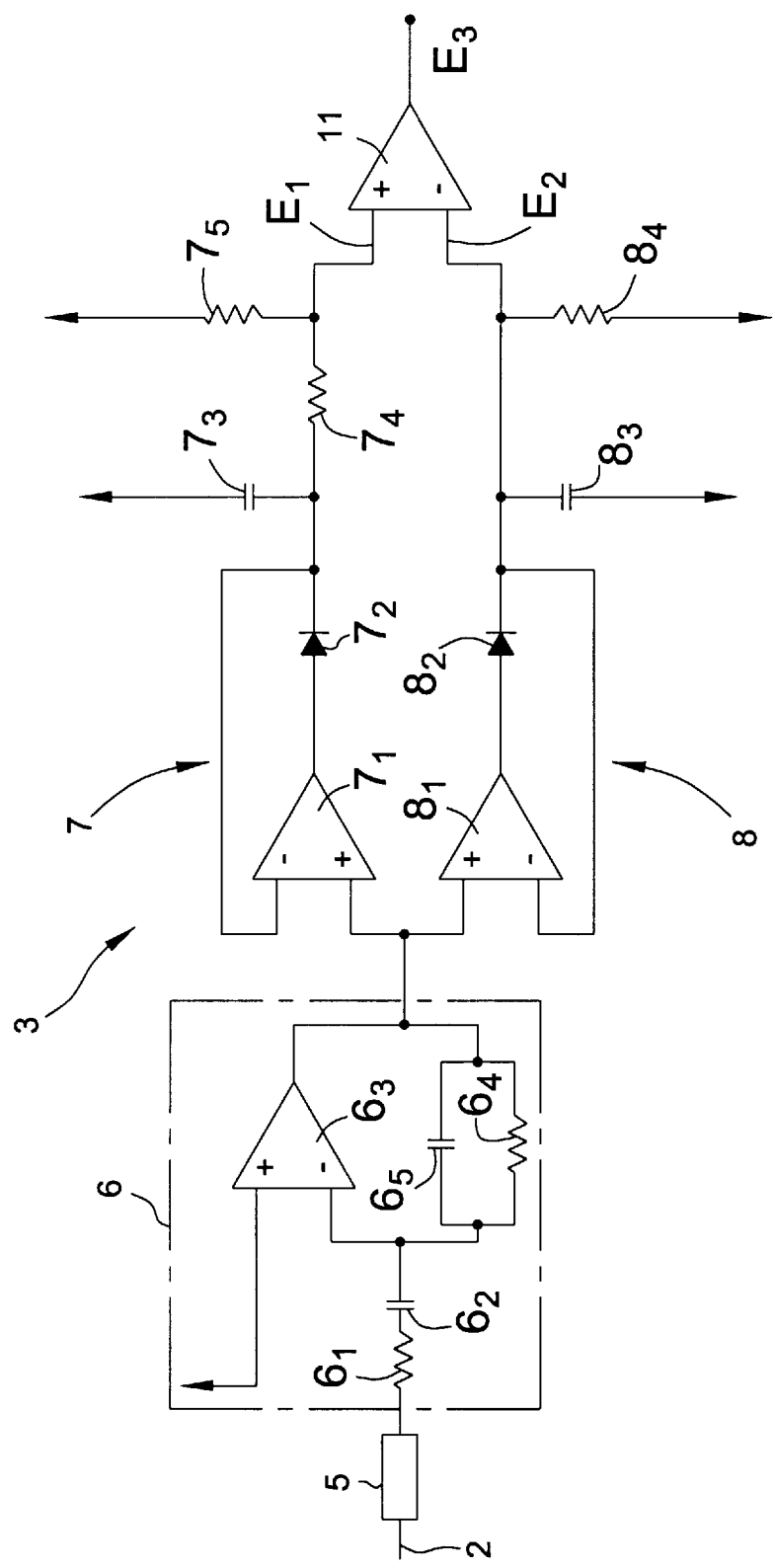
FIG. 2 is a block diagram illustrating a component of the ambulatory module according to the invention.

Processor P also has a counter B connected to pickup and processing unit 3. As shown in FIG. 2, pickup and processing unit 3 has, at the input, an ECG signal filter stage 5. Filter stage 5 has a passband of preferably between 1 and 24 Hz, and preferably between 5 and 16 Hz. The output of filter stage 5 is connected to a circuit 6 that amplifies the alternating component of the signal. Thus, the output of filter stage 5 is connected by a resistor $6_1$ and a capacitor $6_2$ connected in series, at the inverting input of an operational amplifier $6_3$ whose noninverting input is connected to ground. The inverting input of operational amplifier $6_3$ is connected at its output through a circuit composed of a resistor $6_4$ and a capacitor $6_5$ connected in parallel. The output of operational amplifier $6_3$ and hence of stage 6 is connected to two integrators 7 and 8 that have different time constants.

Each integrator 7 and 8 thus has an operational amplifier $7_1$, $8_1$ whose noninverting inputs are connected to the output of filter stage 5 and circuit 6. The inverting inputs of amplifiers $7_1$, $8_1$ are connected to the cathodes of diodes $7_2$, $8_2$ whose anodes are connected to the outputs of the corresponding operational amplifiers. The cathodes of diodes $7_2$, $8_2$ are connected to ground through capacitors $7_3$, $8_3$ connected in parallel respectively with resistors $7_4$, $7_5$, having time constants $\tau_1$, $\tau_2$, respectively, of different values. For example, signal $E_1$ has a time constant of $\tau_1$=3 seconds while signal $E_2$ has a time constant of $\tau_2$=0.2 seconds. The outputs of integrators 7, 8 drive a comparator 11, that at its output, delivers a square-wave signal $E_3$ representing the cardiac cycle.

Figure 3:
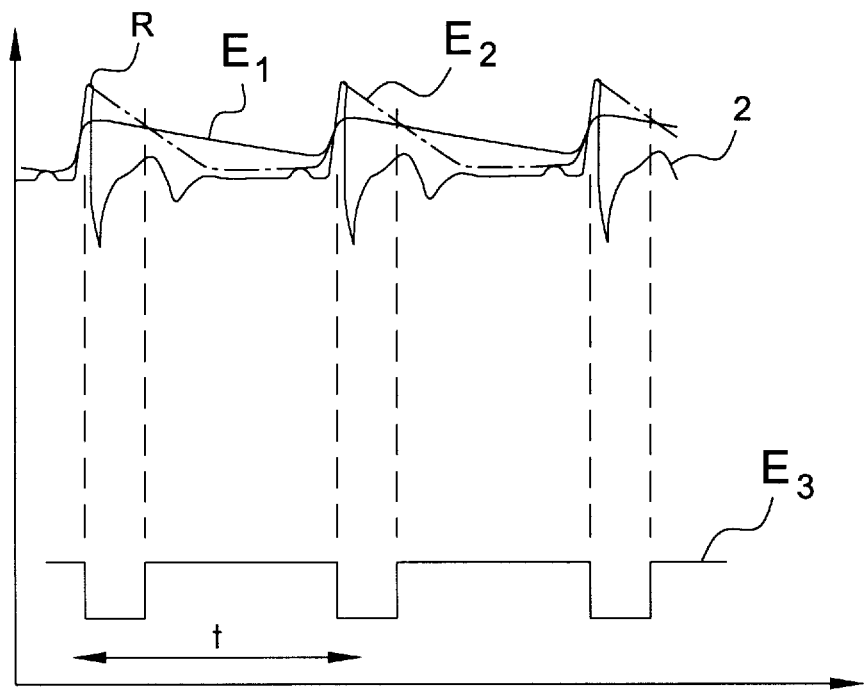
FIG. 3 is a graph showing an example of curves illustrating the heart rate detection principle according to the invention.

As shown in FIG. 3, pickup and processing unit 3 detects peaks "R" of the ECG signal with two signals $E_1$ and $E_2$ that detect the envelope of the signal with different fidelities. Thus, comparator 11 changes from a high level to a low level as soon as signal $E_1$, which has the largest time constant, has reached its maximum value. Comparator 11 retains its low state as long as the value of signal $E_2$ is greater than the value of signal $E_1$. As soon as the value of signal $E_2$ becomes less than the value of signal $E_1$, comparator 11 switches from a low level to a high level. Pickup and processing unit 3 thus enables the peaks "R" of the ECG signal to be detected with great fidelity and hence the heart rate of a person to be detected.

Thus, measurement of each elementary period t separating two consecutive heart pulses, combined with counting the number of peaks or pulses, allows the instantaneous heart rate to be determined. The instantaneous heart rate is obtained by summing the elementary periods t, and dividing this sum by the number of cardiac peaks determined. It should be noted that it is possible to determine this instantaneous heart rate by considering a period T corresponding to a number n×t rather than the elementary period t.

As shown in FIG. 1, processor P has an analog-digital converter ADC connected to a multiplexer 15 whose analog inputs are connected to temperature sensors 4. Multiplexer 15 is controlled by a signal delivered for example by output port E of processor P. According to one aspect of the invention, port E controls a secondary energy source 18 designed to power temperature sensors 4 of any known type.

The portable module 1 described above is used as described below, considering that processor P incorporates an appropriate programming unit to operate it according to the invention.

When processor P is not operating, it is considered to be in a sleep mode when secondary energy source 18 does not supply temperature sensors 4. Processor P incorporates a programming unit for monitoring interruptions that might occur via clock H, pushbutton PB, or computer system O. Prior to running a measurement series, module 1 receives operating parameters from computer system O. This module 1 initialization phase defines recording parameters, namely the measurement recording start and end times as well as the definition of the number n of cardiac periods to be taken into account. Where the latter parameter is concerned, the value n can be selected between 1 and 16, with T=n×t and t being the elementary period between two consecutive pulses. Thus the module offers the advantage of choosing the cardiac cycle selection frequency between values 1 and 16. The higher the value of n, the greater the possible recording time for a given measurement storage capacity. However, by the same token, the measurement is coarser because each cardiac period measured corresponds to an average of n heart pulses. In other words, it may be considered that the module measures the instantaneous heart rate corresponding to the actual instantaneous heart rate, or measures the heart rate with a weighting factor n.

Once the parameters have been recorded, module 1 is ready to check the status of pushbutton PB and read the clock to see whether the data recording start time chosen in the initialization phase has been reached. As soon as the recording period start time has been reached or the pushbutton is pressed, processor P terminates the sleep mode and enters a standby mode waiting for an interrupt generated by the counter and corresponding to a low level of the ECG signal. As soon as the ECG signal low level has been detected, processor P reads a clock time $H_1$ and controls secondary energy source 18 supplying temperature sensors 4. Multiplexer 15 is switched such that it allows selected temperatures to be recorded. As soon as the temperatures have been acquired, secondary energy source 18 is switched so that it no longer supplies sensors 4 with energy. Processor P then enters the sleep mode until there is a further interrupt. As soon as another low level of signal $E_3$ corresponding to the nth pulse after the pulse previously detected appears, the temperature sensor values are acquired and a clock time $H_2$ is read. The difference between values $H_2$ and $H_1$ is then used to determine the time T of a selected cycle. As explained above, the instantaneous heart rate is obtained by dividing time T by the parameter n selected.

The portable module according to the invention allows the instantaneous heart rate to be detected with great accuracy while offering long autonomous operation. Thus, for example, for n=1, it may be possible to make measurements over a period of two months while selection of a higher value for n would multiply the measuring period by that amount.

While the invention has been described in conjunction with specific embodiments thereof, it is evident that many alternatives, modifications and variations may be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A method of recording cardiac activity of a person by using a device delivering an ECG signal and at least one temperature of the patient with the aid of a temperature sensor, the method comprising the steps of:

detecting peaks "R" of the ECG signal with two integrators having different time constants and connected to a comparator delivering a signal ($E_3$) representing cardiac cycles;

recording time (T) of the cardiac cycles to determine the instantaneous heart rate as a function of number of peaks detected; and recording the temperature as soon as the start of the cardiac cycle is detected.

2. The method according to claim 1, further comprising the step of choosing a cardiac cycle selection frequency (n) and recording times of cardiac cycles selected.

3. The method according to claim 1, further comprising the step of supplying energy to the temperature sensor as soon as the start of each cardiac cycle is detected and interrupting it as soon as temperature values are recorded.

4. The method according to claim 1, further comprising the step of filtering the ECG signal wherein passband for such ECG signal is between 1 and 24 Hz.

5. The method according to claim 4, comprising the step of filtering the ECG signal wherein the passband for such ECG signal is between 5 and 16 Hz.

6. A portable module for recording cardiac activity of a person using a device delivering an ECG signal and at least one temperature of the patient using a temperature sensor according to the method of claim 1, comprising:

a main energy source connected to a second energy source supplying temperature sensor through a controlled circuit;

a unit that picks up and processes the ECG signal, having an ECG signal filter stage, connected to two integrators with different time constants, outputs of the integrator being connected to a comparator delivering a signal ($E_3$) representing cardiac cycles;

means for placing the ECG signal pickup and processing unit in operation;

and a processor; said processor comprising;

an analog-digital converter (ADC) for receiving the analog signal delivered by the temperature sensor;

a counter to which the output of comparator is connected to determine the times of the cardiac cycles;

control means allowing the circuit controlling the operation of the secondary source to be controlled and the times of the cardiac cycles and the associated temperature values to be recorded; and means for determining the instantaneous heart rate from the number of peaks detected and the cardiac cycle times.

7. A module according to claim 6, comprising means of selecting recording parameters connected with the cardiac cycles for choosing a cardiac cycle selection frequency (n) and recording the times of the selected cardiac cycles.

8. A module according to claim 7, wherein the recording parameter selecting means allows the cardiac cycle recording times to be chosen from a selection frequency range of 1 to 16 Hz.

9. A module according to claim 6, wherein the means for operating the ECG signal pickup and processing unit includes at least one of a pushbutton and programmed clock.

10. A module according to claim 6, wherein the pickup and processing unit include an ECG signal filtering circuit and wherein a passband for such ECG signal filtering circuit is between 1 and 24 Hz.

11. A module according to claim 10, wherein the passband for said ECG signal filtering circuit is between 5 and 16 Hz.

12. A portable module for recording the cardiac activity of a person using a device delivering an ECG signal and at least one temperature of the patient using a temperature sensor, comprising:

a main energy source connected to a second energy source supplying temperature sensor through a controlled circuit;

a unit that picks up and processes the ECG signal, having an ECG signal filter stage, connected to two integrators with different time constants, outputs of the integrator being connected to a comparator delivering a signal ($E_3$) representing cardiac cycles;

a unit for placing the ECG signal pickup and processing unit in operation;

and a processor; said processor comprising;

an analog-digital converter (ADC) for receiving the analog signal delivered by the temperature sensor;

a counter to which the output of comparator is connected to determine the times of the cardiac cycles;

a control unit allowing the circuit controlling the operation of the secondary source to be controlled and the times of the cardiac cycles and the associated temperature values to be recorded; and a unit for determining the instantaneous heart rate from the number of peaks detected and the cardiac cycle times.

13. A module according to claim 12, comprising a unit to select recording parameters connected with the cardiac cycles for choosing a cardiac cycle selection frequency (n) and recording the times of the selected cardiac cycles.

14. A module according to claim 13, wherein the recording parameter selecting unit allows the cardiac cycle recording times to be chosen from a selection frequency range of 1 to 16 Hz.

15. A module according to claim 12, wherein the unit for operating the ECG signal pickup and processing unit includes at least one of a pushbutton or programmed clock.

16. A module according to claim 12, wherein the pickup and processing unit include an ECG signal filtering circuit and wherein a passband for such ECG signal filtering circuit is between 1 and 24 Hz.

17. A module according to claim 16, wherein the passband for said ECG signal filtering circuit is between 5 and 16 Hz.

* * * * *